United States Patent [19]

Goldstein et al.

[11] 3,998,845

[45] Dec. 21, 1976

[54] EMULSION PROCESS FOR SULFOLENE AND SULFOLANE PRODUCTS

[75] Inventors: Herbert J. Goldstein, White Meadow Lake; Hsiao-Jun Li, Morristown, both of N.J.

[73] Assignee: Texas-U.S. Chemical Company, Parsippany, N.J.

[22] Filed: June 14, 1974

[21] Appl. No.: 479,489

Related U.S. Application Data

[63] Continuation-in-part of Ser. No. 192,634, Oct. 26, 1971, Pat. No. 3,822,286, which is a continuation-in-part of Ser. No. 825,385, May 16, 1969, abandoned.

[52] U.S. Cl. .................................. 260/332.1
[51] Int. Cl.² ................................ C07D 333/48
[58] Field of Search ......................... 260/332.1

[56] References Cited

UNITED STATES PATENTS

| 1,196,259 | 8/1916 | Matthews et al. | 260/332.1 |
| 2,395,050 | 2/1946 | Hooker et al. | 260/327 |
| 2,443,270 | 6/1948 | Robey et al. | 260/329 |
| 2,578,565 | 12/1951 | Mahan et al. | 260/332.1 |

FOREIGN PATENTS OR APPLICATIONS

| 506,839 | 9/1930 | Germany | 260/332.1 |
| 236,386 | 7/1911 | Germany | 260/332.1 |

OTHER PUBLICATIONS

Chemical Rubber Handbook (Chem. Rubber Pub. Co., Cleveland, Ohio, 1962), pp. 876–879, 1030, 1031, 1038, 1039.
McCutcheon, "Detergents & Emulsifiers" (Allured Pub. Co., Ridgewood, N.J., 1970), pp. 87, 94, 95, 149, 194, 202, 243, 255.
Sakashita "Chemical Abstracts" vol. 73 (1970), p. 67490K.
Nikitina "Chemical Abstracts" vol. 72 (1970), p. 32632K.

*Primary Examiner*—James O. Thomas, Jr
*Assistant Examiner*—A. Siegel
*Attorney, Agent, or Firm*—Delmar L. Sroufe; M. Ted Raptes

[57] ABSTRACT

Sulfolene, a typical conjugated diene cyclic sulfone, is prepared by emulsifying butadiene in water in the presence of an antioxidant, and thereafter reacting the emulsion with sulfur dioxide under high pressure, for a period sufficient to complete reaction with the butadiene, whereby yields approaching quantitative are obtained.

9 Claims, No Drawings

EMULSION PROCESS FOR SULFOLENE AND SULFOLANE PRODUCTS

CROSS-REFERENCE TO RELATED APPLICATIONS

The present application is a continuation-in-part of copending application Ser. No. 192,634 filed Oct. 26, 1971 now patent No. 3,822,286 which is a continuation-in-part of Application Serial No. 825,385 filed May 16, 1969, now abandoned.

BACKGROUND OF THE INVENTION

1. Field of the Invention

This invention relates to the production of sulfolene. Sulfolene, or butadiene sulfone, is a well known cyclic monosulfone which has considerable value as a chemical intermediate (and as a source of pure butadiene by thermal decomposition). It can be readily hydrogenated to sulfolane, which is a valuable selective solvent for many organic substances, as well as a thermally stable inert reaction medium.

2. Description of the Prior Art

The conventional method for preparing sulfolene is to mix a large molar excess of liquid butadiene, or the appropriately substituted diene, with liquid sulfur dioxide under non-aqueous conditions, at pressures between 100 and 500 pounds per square inch and at a temperature of about 100° C. The reaction times required under these conditions, that is, without some modification of the process, can be as high as two days. The bulk of the literature as a consequence, is largely composed of reports on optimizing this basic process.

In addition to the problem of extended reaction times, sulfur dioxide and butadiene in the conventional processes also react to form (insoluble) polymeric butadiene sulfones; generally those conditions which increase the reaction rate for the sulfolene reaction also increase the rate for the polymer reaction.

Because of these factors, most of the investigative work on sulfolene, and conjugated diene sulfones has been oriented toward improving the efficiency and yield from the sulfolene reaction. This has resulted in the development of methods involving the use of polymer inhibitors to prevent formation of the polysulfone (U.S. Pat. No. 2,443,270); sodium hydroxide washing of the butadiene to eliminate peroxides, which favor the formation of polymer (U.S. Pat. No. 2,420,834); and various techniques to achieve improved results by accurately controlling the temperature of the reaction (U.S. Pat. Nos. 2,402,891 and 2,395,050). Other procedures describe the preparation of sulfolene in alcohols or other organic substances (U.S. Pat. No. 3,077,479). German Pat. No. 506,839, dated Sept. 16, 1930 teaches that polyfunctional phenols, which may act as stabilizers for styrene and acrolein, inhibit the formation of polymeric sulfones in a reaction between liquid butadiene and liquid $SO_2$ or between these reactants in a mutual solvent, such as benzene. This patent does not teach the aqueous dispersion process nor the inhibiting activity of such materials as mercaptans or inorganic salts of lower valence phosphorous acid, such as $NaH_2PO_2$.

German Pat. No. 236,386 dated July 4, 1911 discloses the fact that butadiene reacts with sulfurous acid in water to give both a crystalline and an amorphous product. It is significant only in showing that butadiene and aqueous sulfurous acid can react. It does not suggest how to prepare the crystalline product in preference to the amorphous product.

A review of the art shows that, for the most part, no significant work has been directed toward developing a new approach to the actual synthesis of sulfolene.

Accordingly, the fundamental object of this invention is to provide a method of preparing sulfolene compounds in substantially improved yields and in shorter times than can be reached with known methods.

SUMMARY OF THE INVENTION

We have discovered that sulfolene can be efficiently produced by reacting sulfur dioxide with an aqueous suspension or emulsion of butadiene in approximately equal molar amounts using a quantity of non-oxygenating water sufficient at least to dissolve all sulfolene formed by the reaction. Conversions in excess of 50% and generally higher than 80% are readily obtained by this process in reaction times ranging from one to three hours. Of the reaction product obtained, 65 to 100% is sulfolene while the remainder is the sulfone polymer. One of the advantages of the aqueous emulsion reaction will be immediately evident, when it is noted that sulfolene is very soluble in hot water, while the polymeric sulfone is very insoluble. Sulfolene dissolves in the aqueous medium virtually as rapidly as formed. The two as a result, can be easily and virtually automatically separated by filtration of the hot aqueous reaction mixture, thereby avoiding any complicated purification procedures or operations. A further advantage of the aqueous process is that the excess sulfur dioxide is readily removed as a gas at the end of the reaction, and none is present in the finished product. This feature is important to the hydrogenation of the sulfolene to sulfolane, as it eliminates the necessity for costly purification process.

PREFERRED EMBODIMENTS

In the aqueous emulsion preparation of sulfolene, the most important step is rendering the water nonoxygenating. Water normally contains dissolved oxygen and, as such, it is "oxygenating" in that it is capable of supplying or imparting active oxygen to materials in contact with such water. By "nonoxygenating water" we mean water which has been treated to prevent its imparting or releasing active oxygen either: (1) by deaeration of the water prior to using it in the system, or (2) as presently preferred, by the addition of an appropriate antioxidant in the water phase of the reaction system. It has been found that the solubility of the antioxidant at the reaction conditions has an important bearing on the yield of sulfolene product. Thus solubility under the proposed reaction conditions is an important factor to be considered in the selection of the antioxidant.

If the water is rendered nonoxygenating by deaeration, any conventional deaeration means may be used, such as purging the water by providing means for intimate contact with a flowing stream or an atmosphere of nitrogen, inert gas, or steam.

In the absence of deaeration or the incorporation of an antioxidant in the process water, the product of the aqueous reaction will contain about 15% sulfolene and 85% polysulfone. If the water is rendered nonoxygenating by deaeration with nitrogen, the product will contain about 65% sulfolene and 35% polymer.

When the water is rendered nonoxygenating by use of an antioxidant in accordance with the presently preferred embodiment of this invention, the sulfolene content is increased to the 80 to 100% level with a corresponding drop in the amount of polysulfone. The presently preferred antioxidants include: Alkyl mercaptan, an inorganic salt of inorganic lower valence sulfur acid, an inorganic salt of inorganic lower valence phosphorous acid, or mixtures thereof. Examples of suitable antioxidants include sodium dithionite, sodium hypophosphite, sodium sulfide, sodium sulfite, n-octyl mercaptans, n-butyl mercaptan. By way of comparison, data are included herein relating to the use of polyfunctional phenols as antioxidants; however, such materials are not preferred in the practice of the present invention because some members of this group are not as soluble in water as the members of the preferred classes of antioxidants. Also, the use of phenols have been curtailed in many industrial plants because of difficulties encountered in processing wastes containing these materials in conventional waste treatment plants. It should be noted that in as much as the sulfolene reaction is conducted under acidic conditions, the selected antioxidant must be able to function in an acid medium. Sodium dithionite and sodium sulfide, are acid unstable compounds which have been found to be exceptions to this requirement, and, as such, are readily applicable for use in the novel process of this invention.

The antioxidants are used at levels of 0.1 to 15 parts per 1000 parts of water charged into the reactor. The preferred level is 2.5 to 7 parts per 1000 parts of water used.

Inasmuch as the water is to be the continuous phase for the reaction system as well as the solvent for the sulfolene product, it is important to precisely establish the proportions of butadiene and water to be used prior to forming the emulsion. The reaction which is used in making this determination is

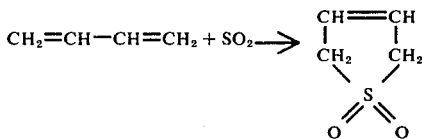

Under optimum conditions, it is feasible to aim for a saturated aqueous solution of sulfolene product. This indicates the initial presence of 80 – 180 parts butadiene per 100 parts of water. It is preferred, however, to operate at about one-fourth to three-fourths of that level in order to maintain complete control over the reactions.

When the sulfur dioxide ingredient is dissolved in water it produces a pH of about 2.0. Thus, the reaction in aqueous systems between sulfur dioxide and butadiene occurs under acidic conditions because of the sulfur dioxide dissolved therein. It is therefore necessary when forming the butadiene emulsion to use an emulsifying agent which functions under acidic conditions. The desired dispersion system may be achieved by the use of from about 0.05% to 1.0%, based on the weight of water, of an emulsifying agent which may be an anionic, cationic, non-ionic, or amphoteric emulsifier. Suitable emulsifiers include sodium lauryl sulfate, sulfonated fatty acid derivatives, sulfonates, sulfates, aliphatic phosphate esters, alkanolamides, heterocyclic acids, substituted sarcosinates, salts of sulfosuccinate derivatives of fatty acids, salts of dodecyl sulfate, salts of alkyl aryl sulfonates, salts of mono- or di-alkyl phosphoric acids, amphoteric salts of fatty acid 2-imidazolinyl compounds, salts of fatty alcoyl sarcosine, fatty acid alkanolamides and polyethoxylated alkyl phenols. Among those found to be especially effective are the following:

| Type | Trade Name | Formula | |
|---|---|---|---|
| Alkylammonium alkylsulfate | Sipex A | $\left[ C_{12}H_{25}-O-\underset{\underset{O}{\|\|}}{\overset{\overset{O}{\|\|}}{S}}-O \right]^{-}$ | $NH_4^+$ |
| | — | $\left[ C_{12}H_{25}-O-\underset{\underset{O}{\|\|}}{\overset{\overset{O}{\|\|}}{S}}-O \right]^{-}$ | $\left[ C_2H_5-\underset{\underset{H}{\|}}{\overset{\overset{H}{\|}}{N}}-C_2H_5 \right]^{+}$ |
| Alkanolammonium alkylsulfate | — | $\left[ C_{12}H_{25}-O-\underset{\underset{O}{\|\|}}{\overset{\overset{O}{\|\|}}{S}}-O \right]^{-}$ | $\left[ HO-C_2H_4-\underset{\underset{CH_3}{\|}}{\overset{\overset{CH_3}{\|}}{N}}-H \right]^{+}$ |
| | Sipex DEA | $\left[ C_{12}H_{25}-O-\underset{\underset{O}{\|\|}}{\overset{\overset{O}{\|\|}}{S}}-O \right]^{-}$ | $\left[ HO-C_2H_4-\underset{\underset{H}{\|}}{\overset{\overset{H}{\|}}{N}}-C_2H_4-OH \right]^{+}$ |
| | Sipex LT6 | $\left[ C_{12}H_{25}-O-\underset{\underset{O}{\|\|}}{\overset{\overset{O}{\|\|}}{S}}-O \right]^{-}$ | $\left[ HO-C_2H_4-\underset{\underset{C_2H_4OH}{\|}}{\overset{\overset{H}{\|}}{N}}-C_2H_4-OH \right]^{+}$ |

| Type | Trade Name | Formula |
|---|---|---|
| Sarcosinate | Sarkosyl O | $CH_3-(CH_2)_7-CH=CH-(CH_2)_7-C(=O)-N(CH_3)-CH_2-C(=O)-OH$ |
| Sarcosinate | Sarkosyl NL-30 | $C_{11}H_{23}-C(=O)-N(CH_3)-CH_2-C(=O)-ONa$ |
| Alkanolamide | Witamide No. 272 | $CH_3-(CH_2)_7-CH=CH-(CH_2)_7-C(=O)-NH-CH_2-CH(OH)-CH_3$ |
| Alkanolamide Sulfosuccinate | Emcol K-8300 | $[CH_3-(CH_2)_7-CH=CH-(CH_2)_7-C(=O)-NH-CH_2-CH(CH_3)-O-C(=O)-CH(-O-SO_2-)-CH_2-C(=O)-O-]Na_2$ |
|  | Emcol F-3250 | $[CH_3-(CH_2)_7-CH=CH-(CH_2)_7-C(=O)-NH-CH_2-CH(CH_3)-O-C(=O)-CH(-O-SO_2-)-CH_2-C(=O)-O-]$ |
| Alkanolammonium alkarylsulfonate | Emcol P10-59 | $[CH_3-CH(OH)-CH_2-NH_3]_2^+$ and $[C_{12}H_{25}-C_6H_4-SO_3^-][CH_3-CH(OH)-CH_2-NH_3^+]$ |
| Alkanolmonoglyceride sulfonate | Sipon MGS100 | $[C_{11}H_{23}-C(=O)-O-CH_2-CH(OH)-CH_2-S(=O)_2-O^-]Na^+$ |
| Sodium lauryl sulfate | Duponol WAQE | $C_{12}H_{25}SO_4\ Na$ |
| Complex organic polyphosphonic ester | Strodex PK-90 | Potassium Salt |
| Heterocyclic acid salt | Miranol C2MSF Conc. Miranol Jem. Conc. | Structure with R-C(=N-CH_2-CH_2-)-N^+(-CH_2-CH_2-O-CH_2COO^-)(-CH_2COO^-); $Na^+$ R=coconut fatty acid; $OH^-$ R=octoic acid |
| Isooctyl phenyl polyethoxy ethanol | Triton X-100 | $CH_3-C(CH_3)_2-CH_2-C(CH_3)_2-C_6H_4-(O-CH_2-CH_2)_{9-10}-OH$ |

The emulsifier is used at levels of 0.5 to 10 parts per 1000 parts of water charged, and the preferred level is 3 to 6 parts.

Although butadiene is the preferred conjugated diene monomer with regard to the process of this invention, other diene monomers may effectively be utilized therein. It is thus appropriate to characterize the applicable diene monomers in terms of the following formula:

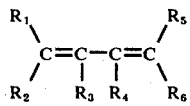

wherein $R_1$, $R_2$, $R_3$, $R_4$, $R_5$ and $R_6$ are independently selected from the group consisting of hydrogen atoms and alkyl, alkenyl, aryl, alkoxy, alkaryl, aralkyl, cycloalkyl, cycloalkenyl and halogen radicals. Among the applicable conjugated diene monomers are included:

butadiene-1,3; 2-methyl butadiene-1,3 (isoprene); pentadiene-1,3 (piperylene); 2,3-dimethyl butadiene1,3; 2,3-diethyl butadiene-1,3; 2,3-di-tertiary-butyl butadiene1,3; 2-tertiary-butyl butadiene-1,3; 1,2,3,4-tetramethyl butadiene-1,3; 1,4-dimethyl-2,3-diethyl butadiene-1,3; 2-methyl pentadiene-1,3; 4-methyl pentadiene-1,3; 2-methyl hexadiene-1,3; 4-ethyl hexadiene-1,3; cyclopentyl butadienes; cyclohexyl butadienes; cyclopentyl hexadienes; 2-phenyl butadiene-1,3; 2-chlorbutadiene-1,3; 2-methyl-3-chlorbutadiene-1,3; 3-methoxybutadiene-1,3; and the like. Needless to say, the use of any of these materials will result in the preparation of the correspondingly substituted sulfolene product, and the term "sulfolene compound" as used herein and in the claims includes the compound "sulfolene" and such substituted sulfolene products. For purposes of this disclosure, statements attributed to butadiene are equally applicable to any of these diene monomers.

EXAMPLE I

In the typical practice of this invention 50 to 1,700 parts, by weight, (1 to 30 moles) of butadiene is dispersed in 1,000 parts, by weight, of water containing 0.5 to 10 parts, by weight, of emulsifying agent, and 0.1 to 15 parts, by weight, of an antioxidant. The dispersal and/or emulsification of the butadiene is carried out under agitation at pressures between 60 and 550 pounds per square inch gauge at about 25° C. The temperature is subsequently adjusted by between 60° C. and 150° C, following which 60 to 1900 parts (1 to 30 moles) of sulfur dioxide are added to the emulsion. The broad and preferred ranges of ingredients and operating conditions for the process are summarized as follows:

|  | Broad Range | Preferred Range |
| --- | --- | --- |
| Water (parts by weight) | 1000 | 1000 |
| Butadiene (parts by weight) | 50 – 1700 | 200 – 1000 |
| Sulfur dioxide (parts by weight) | 60 – 1900 | 250 – 1200 |
| Emulsifier (parts by weight) | 0.5 – 10 | 3 – 6 |
| Antioxidant (parts by weight) | 0.1 – 15 | 2.5 – 7 |
| Reaction Temperature (° C.) | 60 – 150 | 90 – 130 |
| Reaction Pressure (pounds per square inch gauge) | 60 – 550 | 60 – 500 |

The mixture is allowed to react over a period of 1 to 5 hours. At this point, 80 to 100% of the butadiene has been converted to sulfolene. The hot reaction mixture may be filtered to remove the polymer at this point. However, it is preferred to cool the entire reaction mixture gradually to 50° C to 60° C. and to reduce the pressure to 60 to 100 psig. The excess sulfur dioxide is then either vented off or removed by treating the reaction mixture with sodium bicarbonate to form sodium sulfite. At this point the reaction mixture is a yellow slurry. In accord with the preferred procedure, the mixture is then heated to 85° C. and filtered to remove the polysulfone which has formed during the reaction. Pure sulfolene may be recovered by crystallizing it out of solution by cooling the reaction mixture to room temperature or below and the pure sulfolene product is recovered by any separation means such as a centrifuge or filter. The product can further be purified by recrystallizing it from water and/or alcohol a second time. The final product, after separation of the sulfolene solids by means such as filtering, is vacuum dried and stored for future use, or it is hydrogenated to the saturated compound, sulfolane.

The sulfolene produced by this process has excellent storage stability and, as mentioned previously, requires no additional processing to remove residual sulfur dioxide prior to use, as is the case with the compound prepared by conventional non-aqueous methods.

A variation on this method consists in recycling the mother liquor in a semi-continuous process. The efficiency of the recycling variation is improved by the addition of antioxidant to the mother liquor before each cycle begins. For this purpose, it has been found that between 2 and 7 parts of antioxidant provide added protection against the formation of polysulfone.

As mentioned previously, the sulfolene produced by this process can be readily hydrogenated to the saturated form of the molecule. This can be accomplished with a conventional technique using Raney nickel, pelletized supported nickel, palladium oxide, platinum oxide, etc. as catalyst. Generally between 5 to 20% of the catalyst based on the weight of sulfolene will be sufficient to produce satisfactory results. The hydrogenation reaction can be conducted at temperatures between about 25° and 100° C. and at pressures of about 60 psig to about 600 psig. Between 1 to 7 hours and usually about 4 hours, are required to obtain conversions at the 85% level.

The following examples will afford a better understanding of the invention to those skilled in the art.

EXAMPLE II

This example demonstrates the practice of this invention utilizing a variety of antioxidants and emulsifying agents in aqueous and aqueous emulsion systems. The experiments in this sequence of examples also exhibit the use of a number of different temperature and pressure conditions. Their total effect can be judged from the data reported in Tables IA and IB below.

Specifically the data in Table IA illustrates the improvement in sulfolene yield and total conversion in a water system accompanied by water deaeration and/or use of appropriate antioxidants. The data in Table IB illustrates comparable results through the use of emulsion systems with appropriate emulsifiers and antioxidants.

The basic procedure for conducting these experiments involved dissolving the antioxidant and 2.1 grams of emulsifying agent in deaerated redistilled water by heating and then charging the soap solution into a 2,000 milliliter PARR Series 4500 stirred reactor. Liquid butadiene, purified by passing it through an alumina column, was charged into the reactor and the contents were stirred for 15 minutes. Liquid sulfur dioxide was then added to the reactor with stirring. The reactants were heated rapidly to 90° C and then maintained above 90° C. and below 130° C., with stirring, for about 3 hours. The temperature inside the reactor was measured by a Weston dial thermometer, and an iron-constantan thermocouple. The temperature of the heating jacket was measured with an iron-constantan thermocouple.

The pressure inside the reactor increased from 60 psig to a maximum of nearly 400 psig, and then dropped rapidly. Upon conclusion of the reaction, as indicated by the stable lower pressure of about 80 – 100 psig, the reactor was cooled gradually to about 50° to 60° C., during which time the pressure decreased further to about 60 to 80 psig. The reactor was vented to eliminate excess sulfur dioxide and the contents removed.

The reaction mixture was a yellowish slurry. This was heated to 85° C. and stirred until the yellowish color changed gradually to white. The white slurry was then filtered. The residue was digested with hot water and filtered, after which the filtrates were combined. On cooling, white crystals separated. Additional product was obtained by concentrating the mother liquors. The combined product was dried by suction and finally dried over calcium chloride under vacuum.

The water insoluble product, i.e., the butadiene polysulfone, was dried in air and then over calcium chloride under vacuum.

TABLE IA

Reaction of Butadiene and Sulfur Dioxide in Water System

| Run | Water (grams) | Antioxidants Type | Amount (gms.) | Butadiene (gm-mols) | $SO_2$ (gm-mols) | $SO_2$: Butadiene (gm-mols) (ratio) | Peak Pressure (PSIG) | Peak Temp. (°C) | Time (Hrs) | % Conv | % 3-Sulfolene | % polysulfone |
|---|---|---|---|---|---|---|---|---|---|---|---|---|
| 1. | 450 | HQ' | 3 | 3.76 | 3.95 | 1.05 | 490 | 127 | 3 1/2 | 76 | 99 | 1 |
| 2. | 450 | None | — | 3.71 | 3.75 | 1.01 | 400 | 145 | 4 | 78 | 15 | 85 |
| 3. | 450* | None | — | 3.75 | 3.79 | 1.01 | 420 | 120 | 3 5/12 | 83 | 65 | 35 |
| 4. | 450 | HQ' | 3 | 3.71 | 3.75 | 1.01 | 450 | 121 | 3 1/6 | 86 | 99 | 1 |
| 5. | 450 | $Na_2S_2O_4$ | 1 | 3.71 | 4.05 | 1.09 | 510 | 126 | 4 | 87 | 89 | 11 |
| 6. | 450 | $NaH_2PO_2 \cdot H_2O$ | 1 | 3.71 | 3.75 | 1.01 | 500 | 128 | 4 | 85 | 94 | 6 |
| 7. | 300 | HQ' | 2 | 5.55 | 5.60 | 1.01 | 500 | 129 | 4 | 88 | 97 | 3 |
| 8. | 300 | HQ' | 2 | 5.55 | 5.60 | 1.01 | 460 | 125 | 3 3/4 | 90 | 98 | 2 |
| 9. | 200 | HQ' | 2 | 5.55 | 5.60 | 1.01 | 570 | 132 | 3 3/4 | 80 | 99 | 1 |
| 10. | 200 | HQ' | 2 | 5.55 | 5.60 | 1.01 | 530 | 133 | 4 1/6 | 89 | 99 | 1 |

*Freshly deaerated
'Hydroquinone

TABLE IB

Reaction of Butadiene and Sulfur Dioxide in Emulsion System

| Run | Water (grams) | Emulsifier | Antioxidants Type | Amount (gms) | Butadiene (gm-mols) | $SO_2$ (gm-mols) | $SO_2$O Butadiene (gm-mols) (ratio) | Peak Pressure (PSIG) | Peak Temp. °C | Time (Hrs) | % Conv | % 3-Sulfolene | % Polysulfone |
|---|---|---|---|---|---|---|---|---|---|---|---|---|---|
| 1. | 900 | Emcol P1059 | Ionol[1] | 6 | 3.36 | 6.22 | 1.86 | 200 | 44* | 16 | 100 | 32 | 68 |
| 2. | 450 | " | HQ[2] | 3 | 1.98 | 3.28 | 1.66 | 200 | 44* | 16 | — | 80 | — |
| 3. | 450 | " | Thiophenol $+K_2S_2O_8$ | 7 | 2.11 | 3.51 | 1.66 | 100 | 31* | 16 | 39 | 18 | 82 |
| 4. | 450 | " | HQ[2] | 3 | 1.85 | 3.83 | 2.06 | 300 | 100 | 1 1/2 | 85 | 98 | 2 |
| 5. | 450 | " | HQ[2] | 3 | 1.85 | 3.67 | 1.98 | 100 | 45* | 16 | 79 | 97 | 3 |
| 6. | 450 | " | Ionol[1] | 3 | 1.94 | 4.15 | 2.14 | 360 | 100 | 1 | 84 | 74 | 26 |
| 7. | 450 | Witcamide No. 272 | HQ[2] | 3 | 1.85 | 3.13 | 1.69 | 335 | 120 | 3 1/2 | 85 | 99 | 1 |
| 8. | 450 | Emcol | TBC[3] | 3 | 1.85 | 1.87 | 1.01 | 360 | 112 | 3 1/6 | — | 65 | — |

[1]2,6 di-tert-butyl 4-methyl phenol
[2]Hydroquinone
[3]tertiary butyl catechol
*actual temperature rather than peak temperature

TABLE IB

Reaction of Butadiene and Sulfur Dioxide in Emulsion System

| Water (grams) | Emulsifier | Antioxidant Type | Amount (gms.) | Butadiene (gm-mols) | $SO_2$ (gm-mols) | $SO_2$: Butadiene (gm-mols) (ratio) | Peak Pres. (PSIG) | Peak Temp. (°C) | Reaction Time (hrs.) | % Conv. | % Yield of 3-Sulfolene | % Yield of Polysulfone |
|---|---|---|---|---|---|---|---|---|---|---|---|---|
| 450 | Emcol P1059 | $n\text{-}C_8H_{17}SH$ | 3 | 2.11 | 3.01 | 1.43 | 300 | 97 | 1 5/6 | 79 | 95 | 5 |
| 450 | do | $n\text{-}C_8H_{17}SH$ | 3 | 2.23 | 3.95 | 1.77 | 380 | 110 | 1 | 82 | 95 | 5 |
| 450 | do | $Na_2SO_3$ | 3 | 2.11 | 3.33 | 1.58 | 350 | 103 | 1 7/12 | 100 | 42 | 58 |
| 450 | do | $Na_2S\text{-}9H_2O$ | 3 | 2.11 | 3.23 | 1.54 | 370 | 105 | 1 | 94 | 99 | 1 |
| 450 | do | $Na_2S_2O_4$ | 3 | 1.95 | 3.45 | 1.77 | 380 | 120 | 1 3/4 | 92 | 87 | 13 |
| 450 | do | $NaH_2PO_2H_2O$ | 3 | 1.95 | 3.58 | 1.83 | 380 | 123 | 2 | 88 | 97 | 3 |
| 450 | Witcamide No. 272 | $Na_2S_2O_4$ | 1 | 1.87 | 1.83 | 0.98 | 370 | 120 | 4 | 73 | 99 | 1 |
| 450 | do | $NaH_2PO_2\text{-}H_2O$ | 1 | 2.00 | 1.88 | 0.94 | 400 | 130 | 2 1/6 | 81 | 96 | 4 |
| 450 | do | Hydroquinone | 1 | 1.85 | 1.89 | 1.02 | 390 | 117 | 3 1/4 | 78 | 98 | 2 |

TABLE IB

Reaction of Butadiene and Sulfur Dioxide in Emulsion System

| Water (grams) | Emulsifier | Hydroquinone Antioxidant Amount (gms) | Butadiene (gm-mols) | $SO_2$ (gm-mols) | $SO_2$:Butadiene (gm-mols) (ratio) | Peak Pres. (PSIG) | Peak Temp. (°C) | Reaction Time (hrs.) | % Conv. | % Yield of 3-Sulfolene | % Yield of Polysulfone |
|---|---|---|---|---|---|---|---|---|---|---|---|
| 450 | Emcol P1059 | 3 | 2.05 | 2.40 | 1.17 | 310 | 120 | 2 ½ | 81 | 99 | 1 |
| 300 | Emcol P1059 | 2 | 1.67 | 1.91 | 1.14 | 340 | 100 | 1 | 60 | 80 | 20 |
| 450 | Emcol P1059 | 3 | 1.95 | 1.96 | 1.00 | 355 | 120 | 3 ⅓ | 75 | 99 | 1 |
| 300 | Emcol P1059 | 3 | 1.85 | 1.72 | 0.93 | 320 | 100 | 2 ½ | 69 | 91 | 9 |
| 450 | Emcol F32-50 | 3 | 1.86 | 2.06 | 1.11 | 300 | 105 | 1 | 55 | 82 | 18 |
| 450 | Emcol F32-50 | 3 | 1.97 | 1.96 | 1.00 | 360 | 111 | 2 ½ | 62 | 92 | 8 |
| 450 | Emcol K8300 | 3 | 1.95 | 1.83 | 0.94 | 360 | 112 | 3 | 79 | 91 | 9 |
| 450 | Sipex A | 3 | 1.86 | 2.08 | 1.12 | 340 | 110 | 3 ½ | 67 | 90 | 10 |
| 450 | Sipex DEA | 3 | 1.93 | 2.03 | 1.05 | 380 | 122 | 2 ½ | 66 | 86 | 14 |
| 450 | Sipex LT6 | 3 | 1.85 | 1.87 | 1.01 | 390 | 120 | 2 & | 70 | 89 | 11 |
| 450 | Sipon MGS100 Diethylamine | 3 | 2.04 | 1.88 | 0.92 | 320 | 110 | 2 | 73 | 90 | 10 |
| 450 | Laurylsulfate Dimethylethanolamine | 3 | 1.85 | 1.84 | 1.00 | 340 | 113 | 3 | 51 | 86 | 14 |
| 450 | Laurylsulfate | 3 | 1.76 | 1.86 | 1.05 | 390 | 122 | 2 | 70 | 90 | 10 |
| 450 | Triton X-100 | 3 | 1.91 | 1.85 | 0.97 | 400 | 110 | 3 | 66 | 86 | 14 |

TABLE IB

Reaction of Butadiene and Sulfur Dioxide in Emulsion System

| Water (grams) | Emulsifier | Antioxidant Type | Antioxidant Amount (gms) | Butadiene (gm-mols) | $SO_2$ (gm-mols) | $SO_2$:Butadiene (gm-mols) (ratio) | Peak Pres. (PSIG) | Peak Temp. (°C) | Reaction Time (hrs) | % Conv. | % Yield of 3-Sulfolene | % Yield of Polysulfone |
|---|---|---|---|---|---|---|---|---|---|---|---|---|
| 450 | Witcamide No.272 | HQ' | 3 | 1.91 | 1.87 | 0.98 | 390 | 115 | 3 1/6 | 80 | 98 | 2 |
| 450 | " | HQ | 3 | 2.08 | 1.88 | 0.91 | 310 | 128 | 3 1/3 | 92 | 99 | 1 |
| 450 | Sarkosyl O | HQ | 3 | 1.85 | 1.88 | 0.95 | 380 | 115 | 1 2/3 | 76 | 83 | 17 |
| 450 | Sarkosyl NL-30 | HQ | 3 | 2.04 | 1.94 | 0.92 | 360 | 111 | 2 | 68 | 97 | 3 |
| 900 | SF Flake* | HQ | 6 | 3.76 | 3.76 | 1.00 | 520 | 130 | 3 | 69 | 99 | 1 |
| 900 | Duponol WAQUE | HQ | 6 | 3.71 | 3.97 | 1.07 | 520 | 130 | 3 5/6 | 88 | 93 | 7 |
| 900 | Miranol Jem. (Conc.) | HQ | 6 | 3.81 | 3.77 | 0.99 | 500 | 122 | 3 1/2 | 72 | 99 | 1 |
| 900 | Miranol C2MSF (Conc.) | HQ | 6 | 3.71 | 3.75 | 1.01 | 510 | 130 | 3 5/6 | 84 | 99 | 1 |
| 900 | Strodex PK-90 | HQ | 6 | 3.71 | 3.75 | 1.01 | 510 | 125 | 3 1/3 | 80 | 95 | 5 |

'Hydroquinone
*Sodium salt of partially hydrogenated tallow fatty acid.

EXAMPLE III

This Example demonstrates the use of recycled mother liquor in the process of this invention.

The reactions shown in Table II were conducted in the same manner as in Example II. In Experiement 1, the reactants were prepared and charged into the reactor as in Example II. In Experiments 1A through 1F, the mother liquor resulting from Experiment 1 was used as the reaction medium without additional antioxidant being added. An additional 2 grams of hydroquinone were added to the mother liquor of Experiment 2 which, in turn, was used in Experiments 2A through 2E. For Experiments 2F through 2J, the mother liquor resulting from Experiment 2E was used without the use of additional antioxidant. In each of the predominant Experiments (Experiments 1 and 2), the reaction charge contained 450 grams of water and 2.1 grams of Emulsifier EMCOL P1059.

TABLE II

Reaction of Butadiene and Sulfur Dioxide in Emulsion System

| Experiment | Hydroquinone (gms) | Butadiene (gm-mols) | $SO_2$ (gm-mols) | $SO_2$:Butadiene (ratio) | Peak Pres. (PSIG) | Peak Temp. (°C) | Reaction Time (hrs.) | % Conv. | % Yield of 3-Sulfolene | % Yield of Polysulfone |
|---|---|---|---|---|---|---|---|---|---|---|
| 1 | 3 | 3.71 | 3.75 | 1.01 | 320 | 127 | 3 3/4 | 71 | 99 | 1 |
| 1A | — | 3.71 | 3.75 | 1.01 | 450 | 140 | 3 3/4 | 64 | 80 | 20 |
| 1B | — | 3.71 | 3.75 | 1.01 | 380 | 120 | 4 | 94 | 84 | 16 |
| 1C | — | 3.71 | 3.75 | 1.01 | 380 | 120 | 4 | 76 | 90 | 10 |
| 1D | — | 3.71 | 3.75 | 1.01 | 400 | 132 | 4 | 86 | 78 | 22 |
| 1E | — | 3.71 | 3.75 | 1.01 | 460 | 130 | 4 1/6 | 81 | 76 | 24 |
| 1F | — | 3.71 | 3.75 | 1.01 | 400 | 127 | 4 | 83 | 75 | 25 |
| 2 | 3 | 4.10 | 3.40 | 0.83 | 400 | 123 | 3 | 70 | 99 | 1 |
| 2A | 2* | 3.71 | 3.75 | 1.01 | 420 | 130 | 3 1/4 | 90 | 89 | 11 |
| 2B | 2* | 3.71 | 3.78 | 1.02 | 410 | 127 | 3 | 92 | 87 | 13 |
| 2C | 2* | 3.71 | 3.75 | 1.01 | 400 | 125 | 3 1/4 | 87 | 99 | 1 |
| 2D | 2* | 3.71 | 3.75 | 1.01 | 495 | 130 | 3 | 84 | 93 | 7 |
| 2E | 2* | 3.71 | 3.78 | 1.02 | 460 | 133 | 3 1/4 | 89 | 96 | 4 |
| 2F | — | 3.71 | 4.10 | 1.10 | 500 | 132 | 3 | 91 | 93 | 7 |
| 2G | — | 3.71 | 3.86 | 1.04 | 460 | 130 | 3 10/60 | 90 | 99 | 1 |
| 2H | — | 3.71 | 3.82 | 1.03 | 480 | 130 | 3 00/60 | 92 | 92 | 8 |
| 2I | — | 3.71 | 4.05 | 1.09 | 420 | 120 | 3 50/60 | 86 | 99 | 1 |

TABLE II-continued

| | | | Reaction of Butadiene and Sulfur Dioxide in Emulsion System | | | | | | |
|---|---|---|---|---|---|---|---|---|---|
| Experiment | Hydro-quinone (gms) | Butadiene (gm-mols) | $SO_2$ (gm-mols) | $SO_2$: Butadiene (ratio) | Peak Pres. (PSIG) | Peak Temp. (°C) | Reaction Time (hrs.) | % Conv. | % Yield of 3-Sulfolene | % Yield of Polysulfone |
| 2J | — | 3.71 | 3.75 | 1.01 | 480 | 130 | 4 30/60 | 91 | 99 | 1 |

*Grams of hydroquinone in addition to amount present in mother liquor

It is known that diolefinic conjugated hydrocarbons, like butadiene, are relatively insoluble in water. Likewise, as set forth in Kirk-Othmer Encyclopedia Chemical Technology Vol. 13, pp. 417-420, The Interscience Encyclopedia, Inc., N.Y. (1954) states:

"Sulfur dioxide dissolves in water to form the weak acid, sulfurous acid, $H_2SO_3$. At a partial pressure for sulfur dioxide gas of 1 atm., solutions containing 18.5% $SO_2$ by weight are formed at 0° C and 5.1% strength at 40° C. Under practical conditions where solutions are formed most often at 1 atm. total pressure with air or other diluent gases present, concentrations of from only one-third to one-half of these values are obtained."

It is thus seen that both reactants in the instant aqueous dispersion process are relatively insoluble in the water medium, or at best, only partially soluble.

It is believed that the reaction between butadiene and $SO_2$ occurs in a dispersed phase of butadiene/sulfur dioxide/water. The sulfolene is known to dissolve in both the water and dispersed phase. Thus it must partition itself between these two. So, also must any antioxidant added to the water phase. The degree to which the antioxidants dissolve in the two phases is dependent on their independent solubilities in each phase. Thus, in Example II, Table IA, sodium dithionite ($Na_2S_2O_4$) and sodium hypophosphite ($NaH_2PO_2 \cdot H_2O$) are very soluble in hot water. The effect of water solubility of the antioxidant coupled with the effect of water deaeration (run 3, Table IA) show that in this system the antioxidant in the water phase governs the course of the reaction.

The effect of antioxidant solubility in the water phase using emulsifiers is clearly shown by comparing the data of Table IB of the specification. Thus, Ionol (2,6-ditertiary butyl-4-methylphenol) which is a water insoluble stabilizer for styrene and other polymerizable or oxidizable hydrocarbons is less effective than hydroquinone. It is believed that at higher temperatures Ionol becomes more water soluble which accounts for the substantially increased yield of sulfolene at 100° C.

EXAMPLE IV

This Example demonstrates the catalytic hydrogenation of 3-sulfolene prepared according to the process of this invention.

The hydrogenation of 3-sulfolene was conducted in aqueous solution using powdered or pelleted nickel catalyst and was carried out at 60 to 630 psig and at temperatures between ambient (about 25° C) and 60° C. A 2000 ml Parr Series 4500 stirred Reactor and a 450 ml Parr Series 3910 shaker type hydrogenation apparatus were employed.

A Parr Series 4500 stirred Reactor was used for hydrogenations at 100 psig or higher.

The catalyst, 3-sulfolene, water and other ingredients shown in Table III were added to the reactor which was then closed and evacuated with a water pump. After purging the reactants three times with hydrogen, the reaction mixture was stirred or shaken under a hydrogen pressure of 60 psig or higher and at the temperatures and periods of time shown in Table III.

After absorption of the hydrogen ceased, the reactor was opened and the catalyst filtered off. Water was removed by distillation at atmospheric pressure or (for some runs) under a vacuum. The residue was treated with methyl alcohol to cause unreduced 3-sulfolene to precipitate out of the solution. The unreduced 3-sulfolene was removed by filtration, and the alcohol solution was flash distilled to remove the methyl alcohol and water and then the residue was distilled at 136°–138° C. and at a pressure of 3 to 4 mm to obtain pure sulfolane.

Results of these procedures are presented in Table III.

TABLE III

| | | Catalytic Hydrogenation of 3-Sulfolene in Water | | | | | | | |
|---|---|---|---|---|---|---|---|---|---|
| Water (gm) | 3-Sulfolene (gm-mols) | Catalyst Type | (Wt.%) | Additives Type | Gms. | Reaction Temp. (°C) | Initial $H_2$ Press. (PSIG) | $H_2$ absorbed (gm-mols) | Time (Hrs) | % Yield Pure Sulfolane |
| 500 | 0.5 | Powder | 4 | Emcol P1059 | 2 | Ambient | 630 | 0.64 | 1 ½ | 83 |
| 500 | 0.85 | Powder | 10 | — | — | 40–60 | 60 | 0.91 | 4 | 85 |
| 100 | 0.125 | Powder | 10 | — | — | 40–50 | 60 | 0.13 | 3 | 60 |
| 200 | 0.125 | Pellet | 30 | — | — | 40–50 | 60 | 0.13 | 6 ½ | 70 |
| 100 | 0.125 | Pellet | 30 | MgO | 3 | 40–50 | 60 | 0.18 | 5 | 70 |
| 100 | 0.125 | Pellet | 30 | ZnO | 3 | 40–50 | 60 | 0.15 | 5 | 83 |
| 100 | 0.125 | Pellet | 30 | Witcamide | 0.5 | 40–50 | 60 | 0.15 | 6 | 87 |
| 100 | 0.125 | Pellet | 20 | — | — | 40–50 | 61 | 0.15 | 3 ⅔ | 80 |
| 100 | 0.125 | Pellet | 10 | Witcamide | 0.5 | 40–50 | 61 | 0.157 | 16 | 80 |
| 100 | 0.125 | Pellet | 10 | Emcol P1059 | 0.5 | 40–50 | 61 | 0.157 | 16 | 80 |
| 1000 | 3.81 | Powder | 10 | — | — | 50–60 | 300 | 3.7 | 7 ½ | 82.5 |
| 1000 | 3.81 | Powder | 10 | ZnO | 10 | 50–60 | 300 | 3.7 | 8 ⅓ | 80.5 | none (runs 1 and 5, Table IB) at lower temperatures giving only 32% sulfolene at 44° C. compared with 97% sulfolene with hydroquinone at 45° C. This same effect is also apparent but to a lesser extent at higher temperatures (runs 4 and 6, Table IB) where the yields of

EXAMPLE V

This example demonstrates the use of 2-methyl-1,3-butadiene (isoprene) in the process of this invention.

The reactions shown in Table IV were conducted in the same manner as in Example II with the exception that 2-methyl-1,3-butadiene (isoprene) was substituted for the butadiene.

TABLE IV

Reaction of 2-methyl-1,3-butadiene (isoprene) and sulfur dioxide in Emulsion System

| Water (gms) | Emcol P1059 Emulsifier (gms) | Hydroquinone Antioxidant (gms) | Isoprene (moles) | SO$_2$ (moles) | SO$_2$: Isoprene (mole ratio) | Peak Pres. (PSIG) | Peak Temp. (° C.) | Reaction Time (hrs) | % Conversion | % Yield of 3-methyl-3-sulfolene | % Yield of Polysulfone |
|---|---|---|---|---|---|---|---|---|---|---|---|
| 450 | 2.1 | 3 | 1.47 | 1.56 | 1.06 | 220 | 128 | 3 ¾ | 75 | 99 | 1 |
| 450 | — | 3 | 1.47 | 1.56 | 1.06 | 220 | 130 | 3 ¾ | 79 | 99 | 1 |
| 450* | — | — | 1.47 | 1.56 | 1.06 | 200 | 125 | — | 67 | 84 | 16 |
| 450 | — | — | 1.47 | 1.56 | 1.06 | 165 | 129 | 3 ¼ | 85 | 18 | 82 |
| 450 | 2.1 | — | 1.47 | 1.56 | 1.06 | 195 | 130 | 3 ⅓ | 82 | 15 | 85 |

*Freshly deaerated distilled water

In addition to further illustrating the effectiveness of the process of this invention, the data presented in the above table indicates the necessity for utilizing non-oxygenating water such as deaerated water and/or water having an antioxidant therein in order to obtain high yields of sulfolene product in contrast to polysulfone. Thus a comparison between the first three experiments and the last two experiments in Table IV clearly indicates that where the oxygen effect on the system was inhibited, i.e., the first three experiments, high yields of sulfolene product were obtained.

EXAMPLE VI

Comparable results were obtained with pentadiene-1,3 (piperylene) under the same reaction conditions as described in Example V with the exception that the product was liquid.

Summarizing, it is thus seen that this invention provides a novel and efficient process for the preparation of sulfolene and sulfolane products. Variations may be made in proportions, procedures and materials without departing from the scope of this invention as defined in the following claims.

We claim:
1. A method for the preparation of sulfolene compounds by direct condensation of conjugated dienes with sulfur dioxide which comprises the steps of:
   1. selecting a quantity of water for the reaction, and treating said water to render it nonoxygenating by dissolving in said water an antioxidant selected from the group consisting of alkyl mercaptans and thiophenol; inorganic salts or inorganic lower valence sulfur containing acids, and inorganic salts of inorganic lower valence phosphorus acids;
   2. dispersing in said water a conjugated diene monomer corresponding to the formula

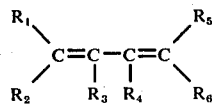

wherein R$_1$, R$_2$, R$_3$, R$_4$, R$_5$, and R$_6$ are independently selected from the group consisting of hydrogen atoms and alkyl, alkenyl, aryl, alkoxy, alkaryl, aralkyl, cycloalkyl, cycloalkenyl and halogen radicals; in an amount from 5 to 170% of the weight of the water medium;
   3. adding to said diene in water dispersion from 6–190% of sulfur dioxide, as based on the weight of water, at a pressure of 60–550 pounds per square inch and a temperature of from 60°–150° C, for 1 to 5 hours to react said sulfur dioxide with said diene dispersion and to produce thereby a reaction mixture comprising a water slurry containing a solution of a sulfolene compound and a polymeric sulfone;
   4. dropping the pressure to ambient levels;
   5. filtering said hot reaction mixture to remove said polymeric polysulfone from said solution containing the sulfolene compound; and
   6. cooling said solution to precipitate sulfolene therefrom and removing the resulting crystals from said solution.

2. The method of claim 1, wherein an emulsifying agent is dissolved in said non-oxygenating water medium in a concentration ranging from about 0.05 to 1%, and said emulsifying agent is selected from the group consisting of: salts of sulfosuccinate derivatives of hydrocarbonyl fatty acids; salts of dodecyl sulfate; salts of alkyl aryl sulfonates; salts of mono- and di-alkyl phosphoric acids; amphoteric salts of fatty acid 2-imidazolinyl compounds; salts of fatty alcoyl sarcosine; fatty acid alkanolamides; and polyethoxylated alkyl phenols.

3. The method of claim 1, wherein said conjugated diene monomer is butadiene-1,3.

4. The method of claim 1, wherein said conjugated diene monomer is 2-methyl butadiene-1,3.

5. The method of claim 1, wherein said conjugated diene monomer is pentadiene-1,3.

6. The method of claim 1, wherein the water medium is separated from the sulfolene compound by filtration and said water medium is utilized as the starting water medium for further practice of the process of claim 1.

7. A method for the preparation of sulfolene by direct condensation of butadiene-1,3 with sulfur dioxide which comprises the steps of:
   1. emulsifying from about 5 to 170% of butadiene-1,3 in a quantity of water containing an emulsifying agent, and containing from about 0.01 to 1.5% of an antioxidant selected from the group consisting of alkyl mercaptans and thiophenol; inorganic salts of inorganic lower valence sulfur containing acids; and inorganic salts of inorganic lower valence phosphorus acids, the butadiene and anti-oxidant concentrations being based upon the weight of the water;
   2. reacting said water and butadiene emulsion to form a slurry containing sulfolene and polymeric sulfone by adding to said emulsion from about 6–190% of sulfur dioxide, based on the weight of water, at a pressure of 60–550 pounds per square inch and a temperature of from 60°–150° C;

3. cooling said reaction mixture and dropping the pressure to ambient levels;
4. heating said slurry to 85° C and filtering said slurry to remove said polymeric polysulfone from said solution; and
5. cooling said sulfolene solution to precipitate said sulfolene and filtering said sulfolene and liquid to separate sulfolene therefrom.

8. The method of claim 7, wherein said emulsifying agent is dissolved in said water in a concentration of from 0.05 to 1% based on the weight of the water and it is an emulsifying agent selected from the group consisting of: salts of sulfosuccinate derivatives of hydrocarbonyl fatty acids; salts of dodecyl sulfate; salts of alkyl aryl sulfonates; salts of mono- and di-alkyl phosphoric acids; amphoteric salts of fatty acid 2-imidazolinyl compounds; salts of fatty alcoyl sarcosine; fatty acid alkanolamides; and polyethoxylated alkyl phenols.

9. A method for the preparation of sulfolane which comprises the steps of:
1. emulsifying from about 5 to 170% of butandiene 1,3 in a quantity of water containing an antioxidant selected from the group, consisting of alkyl thiophenol; inorganic salts of inorganic lower valence sulfur containing acids, and inorganic salts of inorganic lower valence phosphorus acids;
2. reacting said water and butadiene emulsion with from about 6–190% of sulfur dioxide, based on the weight of water, at a pressure of 60–550 pounds per square inch and a temperature of from 60°–150° C to form a slurry containing sulfolene and polymeric sulfone;
3. dropping the pressure to ambient levels;
4. filtering said hot reaction slurry to separate an aqueous solution of sulfolene from said polymeric sulfone and thereafter, cooling said solution to precipitate substantially pure sulfolene therefrom; and
5. hydrogenating a water solution of the sulfolene resulting from step (4) said solution being formed by the mixing of water with said sulfolene and said hydrogenation being conducted in the presence of between 5 and 20% of a hydrogenation catalyst selected from the group consisting of nickel, platinum oxide and palladium oxide at a pressure between about 60 and about 600 psig and a temperature between about 25° and 100° C and filtering catalyst from the solution of water and the sulfolane product; and
6. separating said sulfolane from said water by distillation.

* * * * *

UNITED STATES PATENT AND TRADEMARK OFFICE
CERTIFICATE OF CORRECTION

PATENT NO. : 3,998,845
DATED : December 21, 1976
INVENTOR(S) : Herbert J. Goldstein and Hsiao-Jun Li It is certified that error appears in the above-identified patent and that said Letters Patent are hereby corrected as shown below:

Column 7, line 30, change "by" to read -- to --

Table 1A, close parenthesis in the sixth heading "$SO_2$ (gm-mols)"

Table 1B, Under last line of column 3, after "Emcol" insert
-- P1059 --

Column 11, line 46, change "experiement" to -- experiment --

Column 17, line 23, after "alkyl", insert -- and --

Signed and Sealed this

Thirty-first Day of May 1977

[SEAL]

Attest:

RUTH C. MASON
Attesting Officer

C. MARSHALL DANN
Commissioner of Patents and Trademarks